US00PP15318P2

(12) United States Plant Patent
Smith

(10) Patent No.: US PP15,318 P2
(45) Date of Patent: Nov. 16, 2004

(54) ***CHRYSANTHEMUM* PLANT NAMED 'YOALEXIS'**

(50) Latin Name: *Chrysanthemum×morifolium*
Varietal Denomination: Yoalexis

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/764,869

(22) Filed: Jan. 26, 2004

(51) Int. Cl.[7] ..... A01H 5/00

(52) U.S. Cl. ..... Plt./288

(58) Field of Search ..... Plt./288

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yoalexis', characterized by its upright and somewhat outwardly spreading plant habit; freely branching habit; dense and full plant habit; uniform and freely flowering habit; decorative-type inflorescences with elongated oblong-shaped ray florets; white-colored ray florets; and natural season flowering in early October in the Northern Hemisphere.

2 Drawing Sheets

Botanical classification/cultivar designation: *Chrysanthemum×morifolium* cultivar Yoalexis.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yoalexis'.

The new cultivar is a product of a planned breeding program conducted by the Inventor in Salinas, Calif. and Alva, Fla. The objective of the breeding program is to create new garden-type *Chrysanthemum* cultivars having inflorescences with desirable inflorescence forms, attractive floret colors and good garden performance.

The new *Chrysanthemum* originated from a cross-pollination made in December, 2000 in Salinas, Calif., of a proprietary *Chrysanthemum×morifolium* seedling selection identified as code number 96-L220, not patented, as the female, or seed, parent with a proprietary *Chrysanthemum×morifolium* seedling selection identified as code number 98-M329, not patented, as the male, or pollen, parent. The new *Chrysanthemum* was discovered and selected by the Inventor as a single flowering plant within the progeny of the stated cross-pollination grown in a controlled environment in Alva, Fla. in October, 2001. The selection of this plant was based on its desirable inflorescence form, attractive ray floret color and good garden performance.

Asexual reproduction of the new cultivar by terminal vegetative cuttings in a controlled environment in Alva, Fla. since December, 2001, has shown that the unique features of this new *Chrysanthemum* are stable and reproduced true to type in successive generations.

SUMMARY OF THE INVENTION

The cultivar Yoalexis has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoalexis'. These characteristics in combination distinguish 'Yoalexis' as a new and distinct cultivar:

1. Upright and somewhat outwardly spreading plant habit.
2. Freely branching habit; dense and full plants.
3. Uniform and freely flowering habit.
4. Decorative-type inflorescences with elongated oblong-shaped ray florets.
5. White-colored ray florets.
6. Natural season flowering in early October in the Northern Hemisphere.

In side-by-side comparisons conducted in Alva, Fla., plants of the new *Chrysanthemum* differed from plants of the female parent, the proprietary seedling selection identified as code number 96-L220, in the following characteristics:

1. Plants of the new *Chrysanthemum* were more rounded and flowered more uniformly than plants of the female parent selection.
2. Plants of the new *Chrysanthemum* and the female parent selection differed in ray floret coloration as plants of the female parent selection had white and pink-colored ray florets.

In side-by-side comparisons conducted in Alva, Fla., plants of the new *Chrysanthemum* differed from plants of the male parent, the proprietary seedling selection identified as code number 98-M329, in the following characteristics:

1. Plants of the new *Chrysanthemum* were larger than plants of the male parent selection.
2. Plants of the new *Chrysanthemum* had a more uniform growth habit than plants of the male parent selection.
3. Plants of the new *Chrysanthemum* flowered more uniformly than plants of the male parent selection.
4. Plants of the new *Chrysanthemum* flowered about two to three weeks later than plants of the male parent selection.
5. Inflorescences of plants of the new *Chrysanthemum* had fewer disc florets than inflorescences of plants of the male parent selection.

Plants of the new *Chrysanthemum* can be compared to plants of the *Chrysanthemum* cultivar Linda, disclosed in U.S. Plant Pat. No. 8,294. In side-by-side comparisons conducted in Alva, Fla., plants of the new *Chrysanthemum* differed from plants of the cultivar Linda in the following characteristics:

1. Plants of the new *Chrysanthemum* were larger and more rounded than plants of the cultivar Linda.
2. Plants of the new *Chrysanthemum* flowered more uniformly than plants of the cultivar Linda.
3. Plants of the new *Chrysanthemum* flowered about one week later than plants of the cultivar Linda under natural season conditions.

Plants of the new *Chrysanthemum* can also be compared to plants of the *Chrysanthemum* cultivar Terano, not patented. In side-by-side comparisons conducted in Alva, Fla., plants of the new *Chrysanthemum* differed from plants of the cultivar Terano in the following characteristics:

1. Plants of the new *Chrysanthemum* were larger than plants of the cultivar Terano.
2. Plants of the new *Chrysanthemum* had slightly larger inflorescences than plants of the cultivar Terano.
3. Plants of the new *Chrysanthemum* flowered about one week earlier than plants of the cultivar Terano when grown under natural season conditions.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yoalexis' grown in a container.

The photograph on the second sheet comprises a close-up view of typical inflorescences of the cultivar 'Yoalexis'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Alva, Fla. during the winter in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long night photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Yoalexis.

Commercial classification: Decorative-type garden *Chrysanthemum*.

Parentage:

*Female, or seed, parent.*—Proprietary *Chrysanthemum×morifolium* seedling selection identified as code number 96-L220, not patented.

*Male, or pollen, parent.*—Proprietary *Chrysanthemum×morifolium* seedling selection identified as code number 98-M329, not patented.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded to flattened crown. Stems initially upright, then somewhat outwardly spreading. Freely branching with about nine lateral branches per plant. Moderately vigorous.

*Plant height.*—About 10 cm.

*Plant diameter.*—About 18 cm.

*Lateral branches.*—Length: About 8.5 cm. Diameter: About 2 mm. Internode length: About 1.1 cm. Aspect: Upright and somewhat outwardly spreading. Texture: Pubescent. Color: 146A.

*Foliage description.*—Leaf arrangement: Alternate. Length: About 3.5 cm. Width: About 3.2 cm. Apex: Mucronate. Base: Truncate. Margin: Palmately lobed, sinuses divergent. Texture, upper surface: Slightly pubescent. Texture, lower surface: Pubescent; veins prominent. Color: Developing and fully expanded foliage, upper surface: 147A. Developing and fully expanded foliage, lower surface: 147B. Venation, upper surface: 147A. Venation, lower surface: Close to 147B. Petiole length: About 1.2 cm. Petiole diameter: About 2 mm. Petiole color, upper and lower surfaces: Close to 147B.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. About four inflorescences per lateral branch.

*Flowering response.*—Under natural season conditions, plants flower in early October in the Northern Hemisphere.

*Inflorescence bud (before showing color).*—Height: About 4.5 mm. Diameter: About 6 mm. Shape: Oblate. Color (lower surface of phyllaries): Darker than 146A to close to 147A.

*Inflorescence size.*—Diameter: About 4.2 cm. Depth (height): About 1 cm. Disc diameter: About 1.5 mm; inconspicious. Receptacle diameter: About 2 mm.

*Ray florets.*—Shape: Elongated oblong. Length: About 2 cm. Corolla tube length: About 2 mm. Width: About 5 mm. Apex: Emarginate. Margin: Fused. Texture: Smooth, glabrous; satiny. Surface: Concave to flat. Orientation: Initially upright, then perpendicular to vertical. Number of ray florets per inflorescence: About 120 in numerous whorls. Color: When opening and fully opened, upper surface: Close to 155D. When opening and fully opened, lower surface: Close to 155D.

*Disc florets.*—Shape: Tubular; apex dentate, five-pointed. Length: About 3 mm. Width, apex: About 1 mm. Width, base: Less than 1 mm. Number of disc florets per inflorescence: About 15. Color: Immature: Close to 154A. Mature: Apex: Close to 9A. Mid-section: Close to 144B. Base: Close to 155D.

*Phyllaries.*— Quantity per inflorescence: About 18. Length: About 5 mm. Width: About 2 mm. Shape: Lanceolate. Apex: Acute. Base: Truncate. Margin: Entire. Texture, upper surface: Smooth, waxy. Texture, lower surface: Pubescent. Color, upper surface: Close to 146A. Color, lower surface: Darker than 146A to close to 147A.

*Peduncle.*—Length: First peduncle: About 2.3 cm. Fourth peduncle: About 3.3 cm. Diameter: About 1 mm. Strength: Strong. Aspect: About 35° from vertical. Texture: Pubescent. Color: 146A.

*Reproductive organs.*—Androecium: Present on disc florets only. Anther color: 9A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Yoalexis', as illustrated and described.

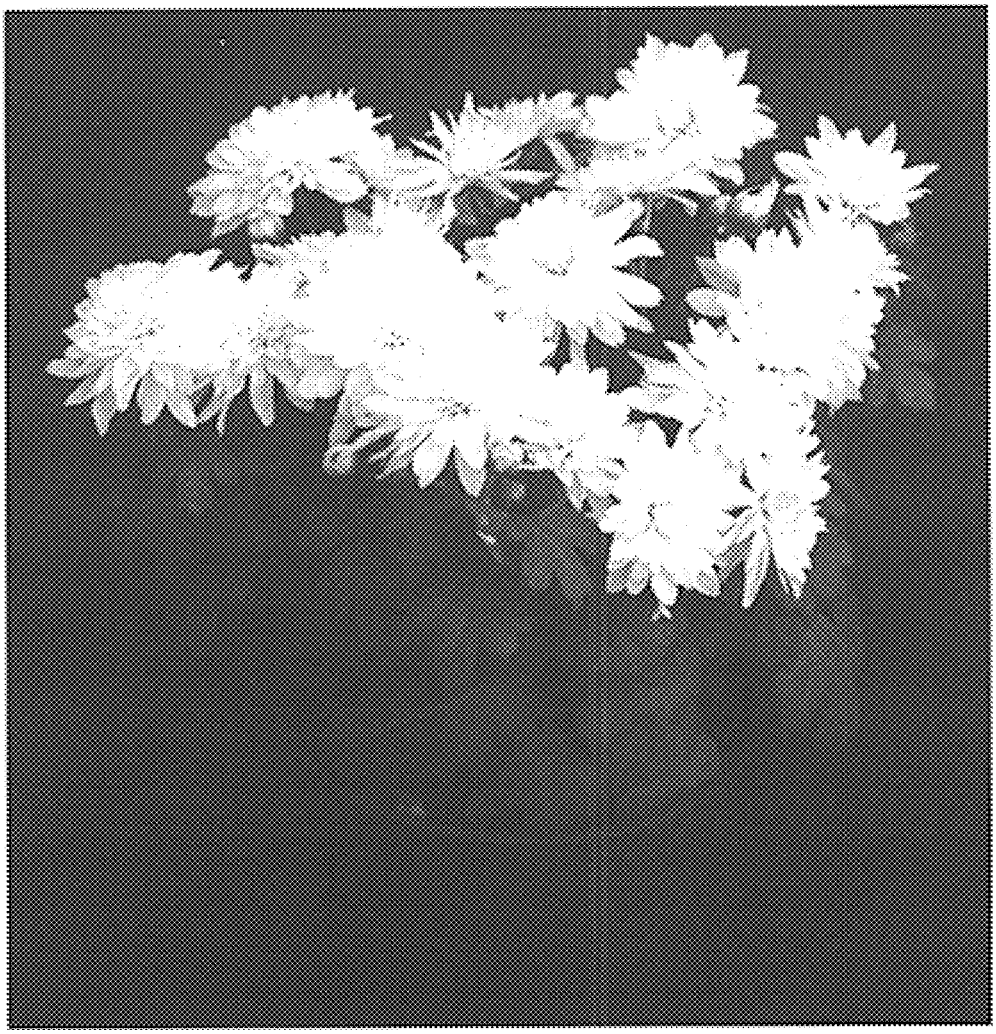

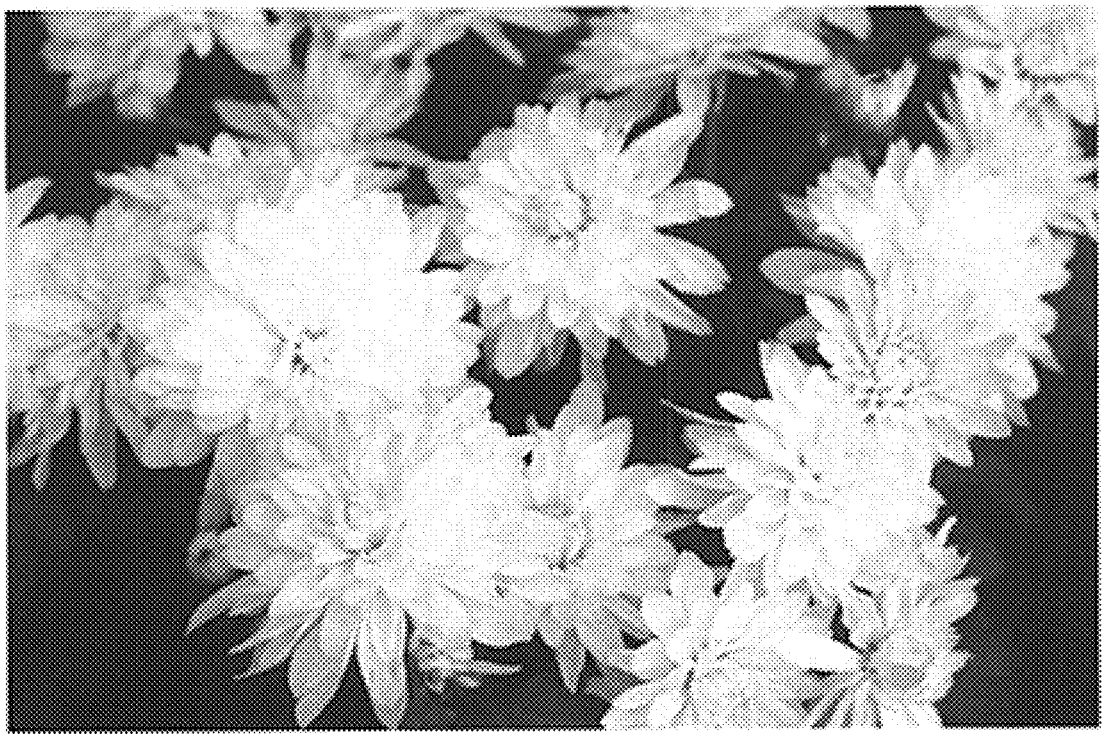

* * * * *